US012629408B2

(12) United States Patent
Rasola et al.

(10) Patent No.: US 12,629,408 B2
(45) Date of Patent: May 19, 2026

(54) PEPTIDES WITH ANTI-TUMOR ACTIVITY

(71) Applicant: UNIVERSITA' DEGLI STUDI DI PADOVA, Padua (IT)

(72) Inventors: Andrea Rasola, Padua (IT); Francesco Ciscato, Cartigliano (IT); Paolo Bernardi, Padua (IT)

(73) Assignee: UNIVERSITÀ DEGLI STUDI DI PADOVA, Padua (IT)

( * ) Notice: Subject to any disclaimer, the term of this patent is extended or adjusted under 35 U.S.C. 154(b) by 713 days.

(21) Appl. No.: 17/431,194

(22) PCT Filed: Feb. 18, 2020

(86) PCT No.: PCT/IB2020/051329
§ 371 (c)(1),
(2) Date: Aug. 16, 2021

(87) PCT Pub. No.: WO2020/170122
PCT Pub. Date: Aug. 27, 2020

(65) Prior Publication Data
US 2022/0111016 A1     Apr. 14, 2022

(30) Foreign Application Priority Data
Feb. 18, 2019     (IT) .......................... 10219000002321

(51) Int. Cl.
| | |
|---|---|
| *C07K 5/10* | (2006.01) |
| *A61K 38/45* | (2006.01) |
| *A61P 35/00* | (2006.01) |

(52) U.S. Cl.
CPC .............. *A61K 38/45* (2013.01); *A61P 35/00* (2018.01)

(58) Field of Classification Search
CPC ...... A61K 38/45; A61P 35/00; C07K 2319/10
See application file for complete search history.

(56) References Cited

U.S. PATENT DOCUMENTS

2013/0078188 A1     3/2013   Tsien et al.

FOREIGN PATENT DOCUMENTS

WO     2013/152193 A2   10/2013

OTHER PUBLICATIONS

Pastorino et al, JBC 277:7610-7618, 2002.*
International Search Report and Written Opinion for corresponding Application No. PCT/IB2020/051329 (mailed Jun. 10, 2020).
Chiara et al., "Hexokinase II Detachment from Mitochondria Triggers Apoptosis throught the Permeability Transition Pore Independent of Voltage-Dependanct Anion Channels," PLOS One 3(3):e1852 (2008).
Ciscato et al., "Displacement of Hexokinase 2 from Mitochondria Induces Mitochondrial CA2 +Overload and Caspase-Independent Cell Death in Cancer Cells," New Therapies XP055636614:A33.2-A33 (2018).
Chen et al., "role of Mitochondira-Associate Hexokinase II in Cancer Cell Death Induced by 3-Bromopyruvate," Biochimica et Biophysica Acta. 1787(5):553-560 (2009).
Ciscato, Francesco, et al., "The Use of Hexokinase 2-Displacing Peptides as an Anti-Neoplastic Approach for Malignant Peripheral Nerve Sheath Tumors," Cells, 13, 1162 (2024).

* cited by examiner

*Primary Examiner* — Mark Halvorson
(74) *Attorney, Agent, or Firm* — Troutman Pepper Locke LLP

(57)     ABSTRACT

The invention concerns an isolated peptide and variants thereof, and therapeutic uses thereof. In particular, such peptides have anti-tumor activity with high selectivity, efficacy and low toxicity. Pharmaceutical compositions comprising the peptides of the invention are also described.

11 Claims, 11 Drawing Sheets

Specification includes a Sequence Listing.

Figura 9B

Figura 10B

SEQUENCE LISTING

```
<160> NUMBER OF SEQ ID NOS: 10

<210> SEQ ID NO 1
<211> LENGTH: 40
<212> TYPE: PRT
<213> ORGANISM: Artificial Sequence
<220> FEATURE:
<223> OTHER INFORMATION: ACPP-HK2 (Activatable Cell Penetrating Peptide
      targeting HexoKinase)
<220> FEATURE:
<221> NAME/KEY: NON_STD
<222> LOCATION: 16
<223> OTHER INFORMATION: beta alanine
<220> FEATURE:
<221> NAME/KEY: NON_STD
<222> LOCATION: 32
<223> OTHER INFORMATION: aminohexanoic acid

<400> SEQUENCE: 1

Met Ile Ala Ser His Leu Leu Ala Tyr Phe Phe Thr Glu Leu Asn Xaa
1               5                   10                  15

Arg Arg Arg Arg Arg Arg Arg Arg Pro Leu Gly Leu Ala Gly Xaa
            20                  25                  30

Glu Glu Glu Glu Glu Glu Glu Glu
        35                  40

<210> SEQ ID NO 2
<211> LENGTH: 40
<212> TYPE: PRT
<213> ORGANISM: Artificial Sequence
<220> FEATURE:
<223> OTHER INFORMATION: SCR control
<220> FEATURE:
<221> NAME/KEY: NON_STD
<222> LOCATION: 16
<223> OTHER INFORMATION: beta alanine
<220> FEATURE:
<221> NAME/KEY: NON_STD
<222> LOCATION: 32
<223> OTHER INFORMATION: aminohexanoic acid

<400> SEQUENCE: 2
```

-continued

```
Val Gly Ala His Ala Gly Glu Tyr Gly Ala Glu Ala Leu Glu Arg Xaa
1               5                   10                  15

Arg Arg Arg Arg Arg Arg Arg Arg Arg Pro Leu Gly Leu Ala Gly Xaa
            20                  25                  30

Glu Glu Glu Glu Glu Glu Glu Glu
        35                  40

<210> SEQ ID NO 3
<211> LENGTH: 40
<212> TYPE: PRT
<213> ORGANISM: Artificial Sequence
<220> FEATURE:
<223> OTHER INFORMATION: ACPP-HK2 variant
<220> FEATURE:
<221> NAME/KEY: NON_STD
<222> LOCATION: 16
<223> OTHER INFORMATION: beta alanine
<220> FEATURE:
<221> NAME/KEY: NON_STD
<222> LOCATION: 32
<223> OTHER INFORMATION: aminohexanoic acid

<400> SEQUENCE: 3

Met Ile Ala Thr His Leu Leu Ala Tyr Phe Phe Thr Glu Leu Asn Xaa
1               5                   10                  15

Arg Arg Arg Arg Arg Arg Arg Arg Arg Pro Leu Gly Leu Ala Gly Xaa
            20                  25                  30

Glu Glu Glu Glu Glu Glu Glu Glu
        35                  40

<210> SEQ ID NO 4
<211> LENGTH: 40
<212> TYPE: PRT
<213> ORGANISM: Artificial Sequence
<220> FEATURE:
<223> OTHER INFORMATION: ACPP-HK2 variant
<220> FEATURE:
<221> NAME/KEY: NON_STD
<222> LOCATION: 16
<223> OTHER INFORMATION: beta alanine
<220> FEATURE:
<221> NAME/KEY: NON_STD
<222> LOCATION: 32
<223> OTHER INFORMATION: aminohexanoic acid

<400> SEQUENCE: 4

Met Ile Ala Ser His Leu Leu Ala Tyr Phe Phe Ser Glu Leu Asn Xaa
1               5                   10                  15

Arg Arg Arg Arg Arg Arg Arg Arg Arg Pro Leu Gly Leu Ala Gly Xaa
            20                  25                  30

Glu Glu Glu Glu Glu Glu Glu Glu
        35                  40

<210> SEQ ID NO 5
<211> LENGTH: 40
<212> TYPE: PRT
<213> ORGANISM: Artificial Sequence
<220> FEATURE:
<223> OTHER INFORMATION: ACPP-HK2 variant
<220> FEATURE:
<221> NAME/KEY: NON_STD
<222> LOCATION: 16
<223> OTHER INFORMATION: beta alanine
<220> FEATURE:
<221> NAME/KEY: NON_STD
<222> LOCATION: 32
<223> OTHER INFORMATION: aminohexanoic acid
```

<400> SEQUENCE: 5

Met Ile Ala Thr His Leu Leu Ala Tyr Phe Phe Ser Glu Leu Asn Xaa
1               5                   10                  15

Arg Arg Arg Arg Arg Arg Arg Arg Arg Pro Leu Gly Leu Ala Gly Xaa
            20                  25                  30

Glu Glu Glu Glu Glu Glu Glu Glu
        35                  40

<210> SEQ ID NO 6
<211> LENGTH: 40
<212> TYPE: PRT
<213> ORGANISM: Artificial Sequence
<220> FEATURE:
<223> OTHER INFORMATION: ACPP-HK2 variant
<220> FEATURE:
<221> NAME/KEY: NON_STD
<222> LOCATION: 16
<223> OTHER INFORMATION: beta alanina
<220> FEATURE:
<221> NAME/KEY: NON_STD
<222> LOCATION: 32
<223> OTHER INFORMATION: aminohexanoic acid

<400> SEQUENCE: 6

Met Ile Ala Ser His Leu Leu Ala Phe Phe Phe Thr Glu Leu Asn Xaa
1               5                   10                  15

Arg Arg Arg Arg Arg Arg Arg Arg Arg Pro Leu Gly Leu Ala Gly Xaa
            20                  25                  30

Glu Glu Glu Glu Glu Glu Glu Glu
        35                  40

<210> SEQ ID NO 7
<211> LENGTH: 40
<212> TYPE: PRT
<213> ORGANISM: Artificial Sequence
<220> FEATURE:
<223> OTHER INFORMATION: ACPP-HK2 variant
<220> FEATURE:
<221> NAME/KEY: NON_STD
<222> LOCATION: 16
<223> OTHER INFORMATION: beta alanine
<220> FEATURE:
<221> NAME/KEY: NON_STD
<222> LOCATION: 32
<223> OTHER INFORMATION: aminohexanoic acid

<400> SEQUENCE: 7

Met Ile Ala Ser His Leu Leu Ala Tyr Tyr Phe Thr Glu Leu Asn Xaa
1               5                   10                  15

Arg Arg Arg Arg Arg Arg Arg Arg Arg Pro Leu Gly Leu Ala Gly Xaa
            20                  25                  30

Glu Glu Glu Glu Glu Glu Glu Glu
        35                  40

<210> SEQ ID NO 8
<211> LENGTH: 36
<212> TYPE: PRT
<213> ORGANISM: Artificial Sequence
<220> FEATURE:
<223> OTHER INFORMATION: ACPP-HK2 II
<220> FEATURE:
<221> NAME/KEY: NON_STD
<222> LOCATION: 28
<223> OTHER INFORMATION: aminohexanoic acid

<400> SEQUENCE: 8

```
Ser His Leu Leu Ala Tyr Phe Phe Thr Glu Leu Asn Arg Arg Arg Arg
1               5                   10                  15

Arg Arg Arg Arg Arg Pro Leu Gly Leu Ala Gly Xaa Glu Glu Glu Glu
            20                  25              30

Glu Glu Glu Glu
        35

<210> SEQ ID NO 9
<211> LENGTH: 38
<212> TYPE: PRT
<213> ORGANISM: Artificial Sequence
<220> FEATURE:
<223> OTHER INFORMATION: ACPP-HK2 III
<220> FEATURE:
<221> NAME/KEY: NON_STD
<222> LOCATION: 30
<223> OTHER INFORMATION: aminohexanoic acid

<400> SEQUENCE: 9

Ser His Leu Leu Ala Tyr Phe Phe Thr Glu Leu Asn Gly Arg Lys Lys
1               5                   10                  15

Arg Arg Gln Arg Arg Arg Gly Pro Leu Gly Leu Ala Gly Xaa Glu Glu
            20                  25                  30

Glu Glu Glu Glu Glu Glu
        35

<210> SEQ ID NO 10
<211> LENGTH: 38
<212> TYPE: PRT
<213> ORGANISM: Artificial Sequence
<220> FEATURE:
<223> OTHER INFORMATION: ACPP-HK2 IV
<220> FEATURE:
<221> NAME/KEY: NON_STD
<222> LOCATION: 30
<223> OTHER INFORMATION: aminohexanoic acid

<400> SEQUENCE: 10

Ser His Leu Leu Ala Tyr Phe Phe Thr Glu Leu Asn His Asp Arg Arg
1               5                   10                  15

Arg Arg Arg Arg Arg Arg Arg Pro Leu Gly Leu Ala Gly Xaa Glu Glu
            20                  25                  30

Glu Glu Glu Glu Glu Glu
        35
```

PEPTIDES WITH ANTI-TUMOR ACTIVITY

This application is a national stage application under 35 U.S.C. § 371 of PCT Application No. PCT/IB2020/051329, filed Feb. 18, 2020, which claims the priority benefit of Italian Patent Application No. 102019000002321, filed Feb. 18, 2019, which are hereby incorporated by reference in their entirety.

FIELD OF THE INVENTION

The invention concerns an isolated peptide and variants thereof, and therapeutic uses thereof. In particular, such peptides have anti-tumor activity with high selectivity, efficacy and low toxicity. Pharmaceutical compositions comprising the peptides of the invention are also described.

STATE OF THE ART

The development of effective antineoplastic treatments requires the identification of molecular characteristics that are selectively necessary for tumor growth. These characteristics would in fact constitute ideal pharmacological targets, allowing the elimination of malignant cells while sparing healthy ones. The result would be the eradication of the tumor in the absence of any side effects.

Unfortunately, at present traditional chemotherapy is acting in a very unspecific way, often causing significant tissue and organ damage, and even the most innovative targeted therapies have so far shown an incomplete and insufficient scope of efficacy. It follows that neoplasms are still the second leading cause of death in the world after cardiovascular problems.

A potential target for the development of antineoplastic treatments is the protein Hexokinase 2 (HK2). In fact, HK2 is either expressed de novo o hyper-expressed in most solid and blood tumors, while it is present only in a limited group of non-tumor tissues. HK2 is associated with the mitochondria of tumor cells, promoting their intracellular replicative metabolism and making them much less sensitive to cell death stimuli, such as chemotherapy and radiation therapy. The presence of this protein has been associated with drug resistance and resistance to radiation therapy in various tumor forms and is essential for tumor development.

Hitting HK2 is potentially an excellent antineoplastic approach. However, the development of molecules that inhibit its function (enzymatic activity) has so far been made impossible by the onset of serious side effects, due both to the fact that HK2 is expressed in important organs (heart, skeletal muscles, kidneys), and the fact that HK2 enzyme inhibitors also block the activity of other enzymes in the hexokinases family, that exert vital functions in all human tissues. Therefore, the HK2 inhibitors studied so far as potential antineoplastic pharmacological treatments (for example the compound 3-bromopyruvate) lack sufficient selectivity, causing side effects that prevent their use, or sufficient efficacy, and have therefore proven to be non-functional.

The aim of the present invention is therefore to provide an antineoplastic treatment suitable for the treatment of tumors that acts selectively and effectively on the protein HK2, without inhibiting the enzymatic activity thereof.

SUMMARY OF THE INVENTION

The invention concerns an isolated peptide that acts as an anti-tumor molecule innovatively conceived and having the sequence of SEQ ID NO:1.

It is a peptide, named ACPP-HK2 (Activatable Cell Penetrating Peptide targeting HexoKinase 2), that selectively targets hexokinase 2 or II (or HK2), a protein strongly expressed in tumor cells. The innovative characteristics compared to current pharmacological approaches are the following: 1. ACPP-HK2 is designed to be activated only in the proximity of tumor cells; 2. once activated, ACPP-HK2 penetrates the tumor cells causing their death in a few minutes; 3. ACPP-HK2 acts without blocking the biological function of the target protein, while causing its intracellular redistribution.

According to another aspect, the present invention relates to the use of the isolated peptide having the sequence of SEQ ID NO:1 or sequence variants thereof, as a medicament.

According to yet another aspect, the present invention relates to the use of the isolated peptide having the sequence of SEQ ID NO:1 or sequence variants thereof, in the treatment of tumors.

Its characteristics as a whole make ACPP-HK2 a potential broad-spectrum, highly selective anti-neoplastic drug with no side effects. Experiments conducted in vitro, in animal models and on primary tumor cells, confirmed these characteristics of ACPP-HK2.

In a further aspect, the invention concerns a pharmaceutical composition comprising an isolated peptide having the sequence of SEQ ID NO:1, or sequence variants thereof, and a pharmaceutically acceptable vehicle.

DESCRIPTION OF THE FIGURES

The invention will now be described in detail and with reference to the attached figures, wherein:

FIG. 6 reports the ex vivo test data as described in Example 4.

FIG. 7 reports the comparison between patient-derived cells (B-CLL) and B lymphocyte from healthy donors (CD19$^+$) after treatment with pepHK2.

NO:1) and those treated with the peptides ACPP-HK2 II (SEQ ID NO: 8), ACPP-HK2 III (SEQ ID NO: 9), and ACPP-HK2 IV (SEQ ID NO:10) at various time periods and concentrations as described in Example 6.

Figure 9A:
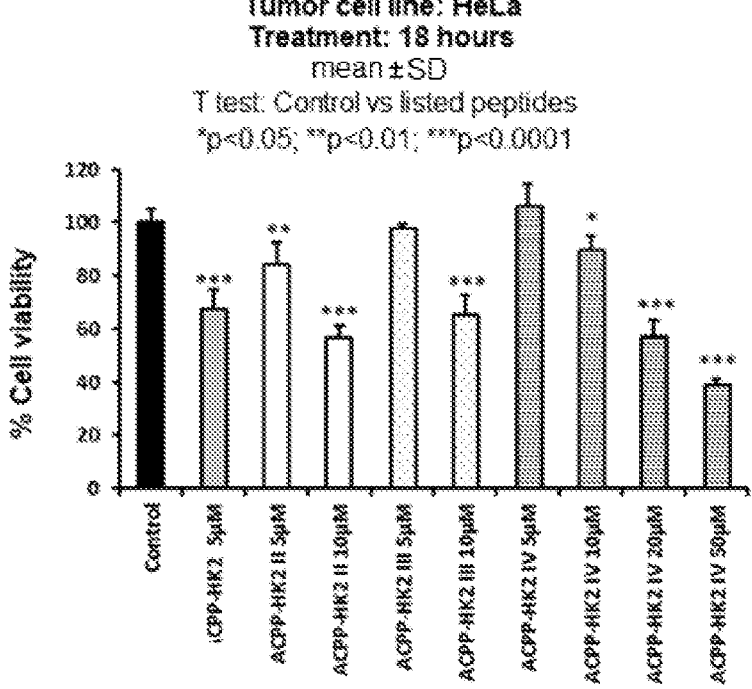
FIG. 9 reports the cell viability comparison between tumor cells treated with the peptide ACPP-HK2 (SEQ ID 3
4
Figure 9A:
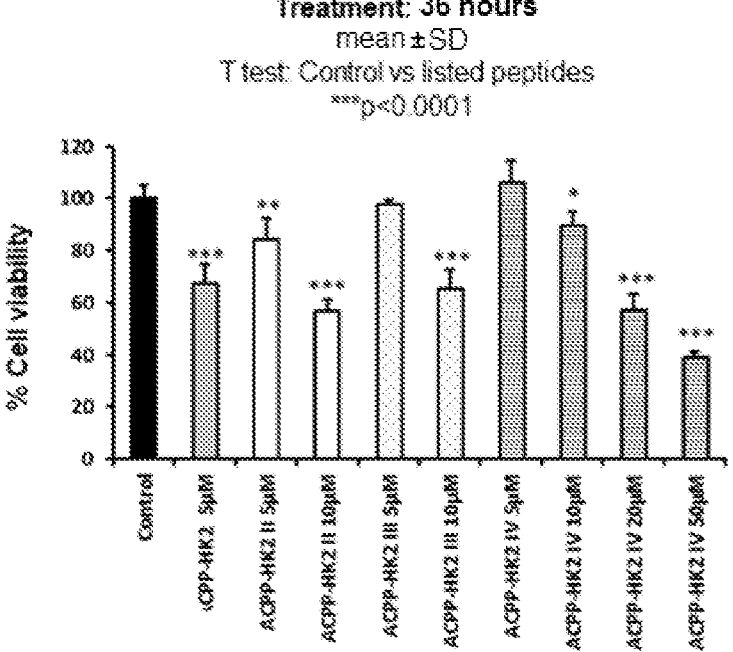

FIG. 9A reports cell viability at 18 hours after treatments with the different isolated peptides.

FIG. 9B reports cell viability at 36 hours after treatments with different isolated peptides.

Figure 10A:
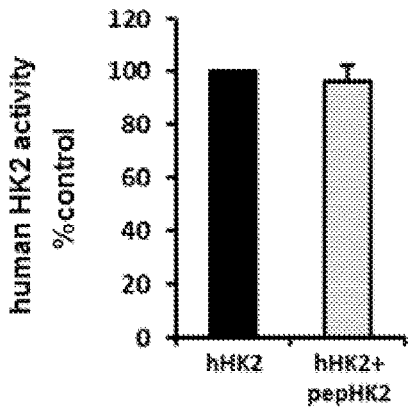
Figure 10A:
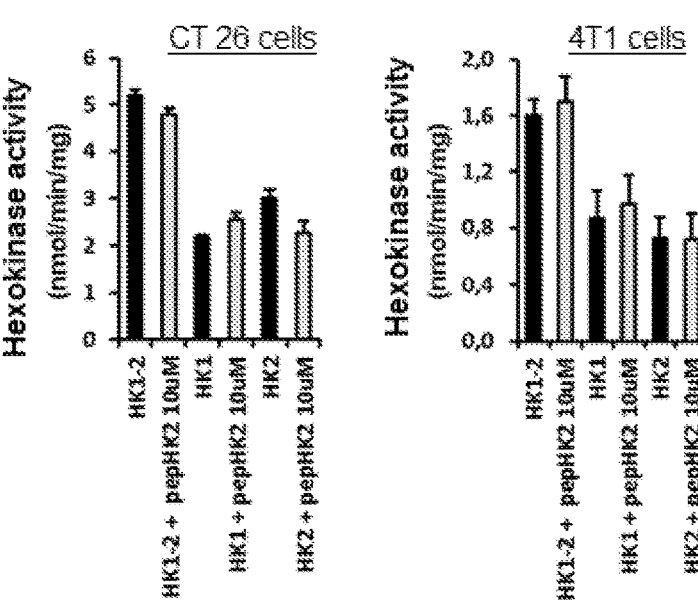

FIG. 10 shows enzymatic activity tests as described in Example 7.

FIG. 10A reports the enzymatic activity of human HK2 measured in the presence or absence of the active form of the peptide ACPP-HK2 (pepHK2).

FIG. 10B shows the enzymatic activity of HK2, HK1 (ubiquitous isoenzyme in the body) and both in the presence or absence of pepHK2 in cell extracts.

Figure 11:
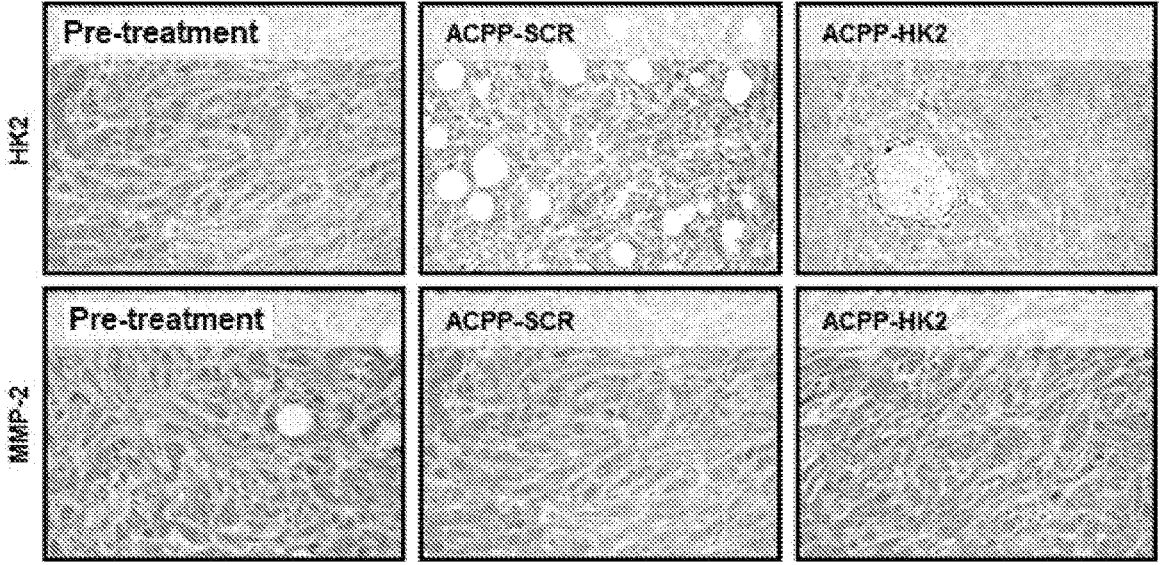

FIG. 11 reports examples of immunohistochemical analysis of tumor samples induced by injecting CT26 cells subcutaneously, as described in Example 2.

DETAILED DESCRIPTION OF THE INVENTION

The invention concerns an isolated peptide having the sequence of SEQ ID NO:1, an anti-tumor molecule conceived in an innovative way.

Advantageously, the structure of the peptide of SEQ ID NO:1 is designed to provide it with specific action, as it activates and becomes permeable through the cell membrane only in the proximity of tumor cells. The activation mechanism exploits the enzymatic action of Matrix Metallo-Proteases (MMP), proteins that are hyper-expressed on the tumor cells membrane or in the tumors' microenvironment, and not expressed, or present in very low amount, in healthy tissues.

As anticipated, the general problems that must be addressed in the development of targeted chemotherapy drugs are systemic toxicity and lack of efficacy.

To date, the known drugs against HK2, and therefore having HK2 as a therapeutic target, have had the disadvantage of inhibiting the important hexokinase enzyme activity even where not necessary. These drugs have therefore been shown to be unable to selectively hit tumor cells, potentially leading to serious side effects.

The present invention develops molecules that are extremely effective in killing tumor cells, as will be shown in the examples, by using a strategy that addresses the problem of selectivity of action against tumor cells:

a. developing molecules selectively directed against a protein, HK2, whose expression is strongly increased in tumors. This constitutes a first conceptual basis for avoiding non-selective toxic effect;

b. designing peptides that do not block the enzymatic activity of HK2, while modifying its subcellular localization. In fact, the peptides of the invention detach HK2 from the mitochondria, intracellular organelles associated with the protein (sufficient condition to trigger cell death). In this way, the enzymatic function of other HK forms, which are found in non-tumor cells, is not affected;

c. designing peptides that can be activated only in the proximity of tumor cells thanks to the following structure: the presence of amino acid sequences for import inside the cells, that are associated both with sequences that shield this import function, and with sequences recognized by proteases of the tumor microenvironment that activate the peptides only in proximity of the tumor, by detaching the screen sequences.

For the aims of the present invention, each peptide has a sequence corresponding to a SEQ ID NO:

SEQ ID NO:1 corresponds to the peptide, named ACPP-HK2 (Activatable Cell Penetrating Peptide targeting HexoKinase 2), having the amino acid sequence: MIASHL-LAYFFTELN βA RRRRRRRRR PLGLAG Ahx EEEEEEEE.

SEQ ID NO:2 corresponds to the SCR control peptide, having the amino acid sequence: VGAHAGEYGAEALER βA RRRRRRRRR PLGLAG Ahx EEEEEEEE (SCR control).

SEQ ID NO:3 corresponds to a variant of the peptide ACPP-HK2, having the amino acid sequence: MIATHL-LAYFFTELN βA RRRRRRRRR PLGLAG Ahx EEEEEEEE.

SEQ ID NO:4 corresponds to a variant of the peptide ACPP-HK2, having the amino acid sequence: MIASHL-LAYFFSELN βA RRRRRRRRR PLGLAG Ahx EEEEEEEE.

SEQ ID NO:5 corresponds to a variant of the peptide ACPP-HK2, having the amino acid sequence: MIATHL-LAYFFSELN βA RRRRRRRRR PLGLAG Ahx EEEEEEEE.

SEQ ID NO:6 corresponds to a variant of the peptide ACPP-HK2, having the amino acid sequence: MIASHL-LAFFFTELN βA RRRRRRRRR PLGLAG Ahx EEEEEEEE.

SEQ ID NO:7 corresponds to a variant of the peptide ACPP-HK2, having the amino acid sequence: MIASHL-LAYYFTELN βA RRRRRRRRR PLGLAG Ahx EEEEEEEE.

SEQ ID NO:8 corresponds to the variant ACPP-HK2 II of the peptide ACPP-HK2, having the amino acid sequence: SHLLAYFFTELN-RRRRRRRRR-PLGLAG-Ahx-EE-EEEEEE, such 36-amino acid peptide has a 90% sequence identity with the sequence of ACPP-HK2 (SEQ ID NO:1), 4/40 amino acids are different.

SEQ ID NO:9 corresponds to the variant ACPP-HK2 III of the peptide ACPP-HK2, having the amino acid sequence: SHLLAYFFTELN-GRKKRRQRRRG-PLGLAG-Ahx-EE-EEEEEE, such 38-amino acid peptide has a 77.5% sequence identity with the sequence of ACPP-HK2 (SEQ ID NO:1), 9/40 amino acids are different.

SEQ ID NO:10 corresponds to the variant ACPP-HK2 IV of the peptide ACPP-HK2, having the amino acid sequence: SHLLAYFFTELNHD-RRRRRRRRR-PLGLAG-Ahx-EE-EEEEEE, such 38-amino acid peptide has a 87.5% sequence identity with the sequence of ACPP-HK2 (SEQ ID NO:1), 5/40 amino acids are different.

The peptide ACPP-HK2 of SEQ ID NO:1, is composed of four functional units, each formed by a short amino acid sequence:

1. A polycationic portion or "cell penetrating sequence" that allows a rapid passage of ACPP-HK2 through the cell membrane. Said portion is composed of a sequence of Arginine (R) ranging from the amino acid in position 17 to the one in position 25 of SEQ ID NO:1;

2. A target sequence for MMPs, the "cleavable sequence", that allows ACPP-HK2 to be activated exclusively in the tumor microenvironment, composed of a stretch of 6 amino acids, from the one in position 26 to that in position 31 of SEQ ID NO:1;

3. A polyanionic sequence that shields the previous poly-cationic sequence, preventing the random entry of ACPP-HK2 into non-neoplastic cells. This shield function is performed by a sequence of glutamic acid (E) from the amino acid in position 33 to the one in position 40 of SEQ ID NO:1 and is eliminated upon cutting by MMPs in the proximity of tumor cells;

4. The active portion, a peptide of the human HK2 protein that turns endogenous HK2 away from the tumor cells mitochondria by competing with the protein itself for interaction with the mitochondria. This unit is composed of a sequence of 15 amino acids, from the amino acid in position 1 to the one in position 15 of SEQ ID NO:1. The active portion is responsible for cell death and is the peptide most important portion.

The invention was designed to have a high degree of flexibility. In fact, it is possible to vary the amino acid sequence of some regions, particularly the sequence recognized by MMPs, to allow them to better adapt to the type of tumor and/or the site where it developed. This special flexibility, that is not present in traditional chemotherapy agents, allows to create groups of specific peptides for highly targeted and selective antineoplastic therapies.

The amino acids of SEQ ID NO:1 and variants thereof, being chiral molecules, can have two different configurations; in fact, each amino acid exists as two enantiomers.

In a preferred form, the peptide of the present invention is a sequence variant of the sequence described by SEQ ID NO:1, it can vary and have an amino acid sequence having up to 70%, 75%, 80%, 85%, 90%, 91%, 92%, 93%, 94%, 95%, 96%, 97%, 98% or 99% sequence identity with SEQ ID NO:1.

The sequence variants can vary, for example, in the sequence of the polycationic portion. In SEQ ID NO:1, this sequence is 9 or 11 amino acids long. This sequence can be longer or shorter and can be modified as there is a number of polycationic (or amphipathic) sequences of varying length and amino acid composition that penetrate through the plasma membrane, as described in Borrelli et al. Table number 1 (Molecules. 2018 Jan. 31; 23(2)). The preferred sequences are between 6 and 16 amino acids in length.

The variants of SEQ ID NO:1 can differ, for example, in the sequence that makes the molecule capable of releasing the effector portion (consisting of polycation+HK2 sequence) specifically in the tumor microenvironment. In SEQ ID NO:1, this is the consensus sequence for cutting by MMPs 2 and 9, and it is 6 amino acids in length. A different consensus sequence may be used for a different extracellular protease, providing the invention with the plasticity necessary to be effective in various tumor microenvironments, characterized by a heterogeneous expression of matrix proteases. For example, the Kallikrein 3 protease, also called PSA (Prostate-Specific Antigen) is hyper-expressed only in prostate cancer (it acts, in fact, as a diagnostic and prognostic biomarker); therefore Kallikrein 3 could be an excellent candidate for the specific release of the peptide active portion exclusively in prostate tumor tissue.

The 9 amino acid-polyanionic sequence of SEQ ID NO:1, which avoids nonspecific accumulation of the peptide by shielding the polycationic sequence, can have longer or shorter variants. However, these variants should maintain the essential constraint of counterbalancing charges of the corresponding polycationic sequences, to prevent the non-specific entry of variants of the isolated peptide SEQ ID NO:1 into the cells. If this requirement is not met by the variants of the polyanionic portion, the corresponding polycationic portions could cause the entire structure of SEQ ID NO:1 (and variants) to penetrate into any cells, even non-tumor cells, and the treatment could therefore be toxic.

The active sequence portion, in this case the 15 amino acids of HK2 of SEQ ID NO:1, mainly hydrophobic, can work with a few more or less amino acids. Due to the chemical characteristics of the sequence, some amino acids could be replaced by others, very similar (e.g. Y with F and vice versa; S with T and vice versa; I with L and vice versa and E with D). Some variants of SEQ ID NO:1 are described in SEQ ID NO:3, SEQ ID NO:4, SEQ ID NO:5, SEQ ID NO:6 and SEQ ID NO:7, SEQ ID NO:8, SEQ ID NO:9 and SEQ ID NO:10. The peptides that have shown better activity are the peptides of SEQ ID NO:1, SEQ ID NO:8, SEQ ID NO:9 and SEQ ID NO:10.

SEQ ID NO:1 has two modified amino acids: the amino acid in position 15 is a beta-alanine, while the amino acid in position 32 is an aminohexanoic acid (Ahx). These two modified amino acids are not essential and act as spacers between the portions. The sequence variants may lack of the two spacing sequences.

According to another aspect, the present invention relates to the use of the isolated peptide having the sequence of SEQ ID NO:1, or sequence variants thereof, as a medicament.

Already at low concentrations, the active portion of the molecule is able to kill a tumor cell in a few minutes (3 to 15 minutes). This rapidity of action is not present in current or potential anti-tumor treatments.

According to yet another aspect, the present invention relates to the use of the isolated peptide having the sequence of SEQ ID NO:1, or sequence variants thereof, in the treatment of tumors.

HK2 has been found to be located in a particular region within tumor cells, i.e. specific portions of the mitochondria, where it inhibits the signals that lead to the death of these cells. We therefore hypothesized that removal of HK2 from this specific intracellular region could lead to death of neoplastic cells.

In a preferred form, the present invention relates to the use of the isolated peptide having the sequence of SEQ ID NO:1, or sequence variants thereof, for use in the treatment of tumors wherein said tumors are solid or liquid tumors.

In an even more preferred form, the present invention relates to the use of the isolated peptide having the sequence of SEQ ID NO:1, or sequence variants thereof, for use in the treatment of tumors selected from the group consisting of colon cancer, breast cancer, leukemia, cervical uterine cancer, plexiform neurofibroma, malignant tumor of the peripheral nerve sheath, schwannoma, and hepatocarcinoma.

In yet another preferred form, these tumors are HK2-expressing tumors.

Metalloproteases, and particularly MMP 2 and 9, are expressed in metastases. The ACPP-HK2 peptide of SEQ ID NO:1 and variants thereof, has the consensus sequence for MMP 2 and 9 and may therefore be used for the treatment of metastatic tumors.

The ACPP-HK2 peptide of SEQ ID NO:1 has anti-tumor cytotoxic action because it is capable of displacing its target, the HK2 protein, from the mitochondria without inhibiting its enzymatic activity.

Surprisingly, the peptide of SEQ ID NO:1, ACPP-HK2, allows:

a) specific release of the active portion (peptide) of HK2 protein in the proximity of the neoplastic cells (both of the primary and the metastatic tumor mass);

b) penetration through the cell membrane;

c) rapid killing of tumor cell.

Our research has shown that this invention, together with the proper administration protocol, kills target cells quickly. We have observed that ACPP-HK2 is effective in reducing the solid tumor growth in laboratory animals already from the first day of treatment and has a rapid cytotoxic action also on human B-cell type chronic lymphocytic leukemia (B-CLL) cells. In addition, ACPP-HK2 is non-toxic in healthy organs and tissues, as shown by histological analyses on laboratory animals.

In a further aspect, the invention relates to a pharmaceutical composition comprising an isolated peptide having the sequence of SEQ ID NO:1, or sequence variants thereof, and a pharmaceutically acceptable vehicle.

In a preferred embodiment, the composition according to the present invention is in a solid or liquid form.

Advantageously in a preferred embodiment, the composition according to the present invention is for enteral and parenteral administration, by intravenous, intraperitoneal, oral, sublingual, aerosol, inhalation, spray, rectal, intraocular, topical, or transdermal administration routes.

Surprisingly, the characteristics of the peptide of SEQ ID NO:1 prevent the cytotoxic portion from being aspecifically released into healthy tissues. The ACPP-HK2 design has the following advantages over other chemotherapy approaches currently in use:

a) it confers specificity of action against the tumor, thus limiting and potentially abolishing the toxicity side effects that characterize classic chemotherapy;

b) the peculiar activation and the system to penetrate the ACPP-HK2 cell guarantee a continuous flow thereof towards the inside of the tumor cell until cell death is induced;

c) in the membrane of tumor cells there are active mechanisms that carry the classic chemotherapy agents outside the cell, thus reducing their intracellular concentration and as a result their efficacy. Given the larger size and the peculiar peptide structure, ACPP-HK2 is not subject to the action of these mechanisms;

d) ACPP-HK2 kills tumor cells within minutes by activating a process called apoptosis. The induction of apoptosis allows tumor cells hit by the peptide to be removed quickly and selectively without activating any inflammatory process that could have secondary toxic effects;

e) thanks to the specific activation system and its weight of about 5000 Da, the peptide does not enter the cells responsible for transformation and inactivation of exogenous molecules (e.g. in the liver cells, as it happens in many cases for classic chemotherapy agents), nor it is recognized by the immune system; these two features together minimize the degradation of ACPP-HK2 after its administration, thereby maximizing its efficacy.

The result is a tool capable of targeting tumor cells very quickly and selectively, which establishes a totally innovative anti-neoplastic approach in terms of mechanism of action and molecular structure of the invention.

This invention may represent a potential first-line drug for the treatment of tumors still lacking an effective cure (e.g. hepatocarcinoma, pancreatic cancer, etc.) and obviously for all tumor forms that express HK2. It could also become an effective second-line drug in case of tumors acquiring resistance to current anti-tumor treatments (e.g. cases of B-cell type chronic lymphocytic leukemia resistant to Rituximab which hyper-express HK2 compared to Rituximab-sensitive patients).

This invention has multiple applications ranging from the treatment of solid tumors to blood tumors. The peptide molecular structure makes it very versatile and flexible, with the concrete possibility of performing personalized treatments depending on the patient and the type of tumor.

The invention was made and tested on multiple in vitro tumor models that demonstrate its transversal efficacy.

We also carried out in vivo studies showing that the invention is effective in the treatment of solid tumors. The autopsy of laboratory animals and the histological examination of the internal organs show no signs of (cyto)toxicity in healthy tissues. From ex vivo studies on human tumor cells isolated from a leukemic patient, the reactivity and efficacy of the invention against these tumor cells and the poor or absent toxicity towards the non-pathological cellular counterpart are evident.

Finally, from our in vivo data it appears that the expression of HK2 and MMPs is not reduced by treatment with the peptide. This indicates that tumor cells do not undergo adaptation forms capable of compromising the efficacy of the peptide.

In a further embodiment, the present invention relates to a method for the treatment of tumors by using the peptide of SEQ ID NO:1 or one of the sequence variants thereof.

Such a method is for the treatment of solid or liquid tumors, preferably tumors selected from the group consisting of colon cancer, breast cancer, leukemia, cervical-uterine cancer, plexiform neurofibroma, malignant tumor of the peripheral nerve sheath, schwannoma, and hepatocellular carcinoma.

In particular said tumors may be tumors that express type II hexokinases, and metastatic tumors.

Examples of embodiments of the present invention are given below for illustrative purposes.

EXAMPLES

Example 1

Synthesis of the Peptide and Sequence Variants Thereof

The peptides of SEQ ID NO:1-SEQ ID NO:7 were synthesized.

Some peptides were synthesized with different combinations of enantiomers. In particular, the peptides of SEQ ID NO:1 with Arginine (R) amino acids of the polycationic sequence in the conformation "D" or in the conformation "L", and all glutamic acid (E) amino acids of the polyanionic sequence in the "D" or "L" conformations, alternating or not with respect to the polycationic sequence.

The peptides were produced with an automatic multiple synthesizer using a so-called solid phase synthesis procedure that provides a resin as a support for amino acid chain elongation. After the synthesis, the peptides are detached from the resin and purified by reverse phase high performance liquid chromatography (H PLC) until at least 95% purity is obtained. Molecular mass analysis was performed using a MALDI-TOF mass spectrometer.

Example 2

Figure 1:
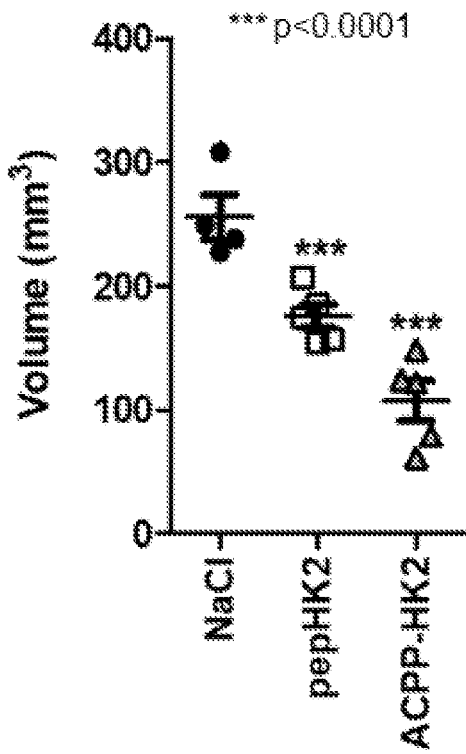
FIG. 1 reports the graph showing the tumor volume evaluation results after treatment of tumors as described in Example 2.
Figure 2:
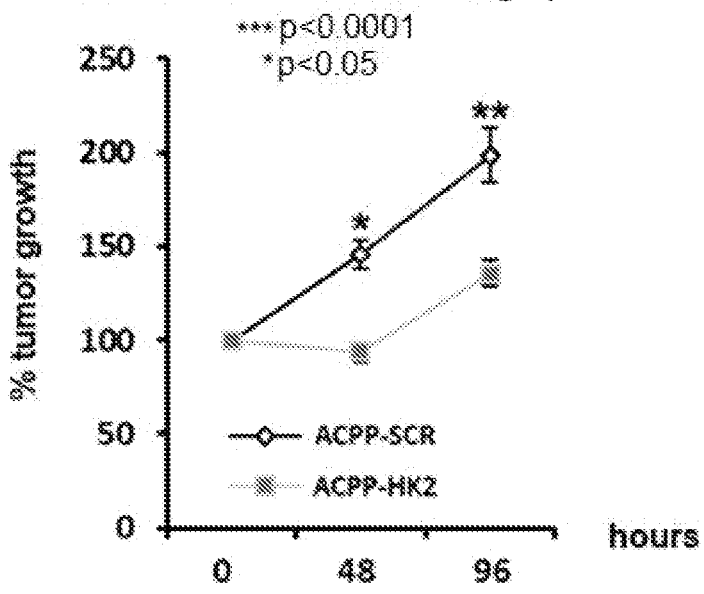
FIG. 2 reports the graph obtained by monitoring tumor growth after systemic treatment with the isolated peptide having the sequence of SEQ ID NO:1.

In Vivo Tests: Colon Cancer 100,000 tumor cells from the murine colon carcinoma line CT26 were injected subcutaneously (in the right flank) to male Balb/c mice. The transplanted cells give rise to a subcutaneous tumor clearly visible from the outside in just over a week. Using this in vivo tumorigenesis procedure, we conducted three different experiments (described below) whose results are represented in FIGS. 1, 2 and 3.

At 8 days post-cell inoculation, the mice were divided into three groups (FIG. 1) and saline boluses (NaCl) without any other solute, or containing the active form of ACPP-HK2 resulting from the proteolytic cut (pepHK2, 2 nmol/injection), or finally containing the entire ACPP-HK2 (2 nmol/injection) were injected into the tumors. Each bolus consisted of 20 µl solution and was injected every 12 hours up to 60 hours. 72 hours after the start of the treatment, the mice were sacrificed, and the tumor volume was measured. In this experiment, ACPP-HK2 was found to be more effective although both the already active form of the peptide (pepHK2) and our invention (ACPP-HK2) reduce tumor growth.

In a second experiment, at 8 days post-cell inoculation the mice were divided into two groups that were administered the ACPP-HK2 peptide or a very similar, but inactive towards HK2 (Activatable Cell Penetrating Peptide Scramble, ACPP-SCR), peptide structure, including experimental negative control function. These data are shown in FIG. 2. Administration was performed every 12 hours by means of intraperitoneal injections of 500 µl each containing 30 nmoles of peptide (ACPP-HK2 or ACPP-SCR). The peptides reach the systemic circulation and hence the tumor through the lymphatic system. Every 48 hours the size of the tumors was measured externally, and their volumes calculated. After 48 and 96 hours, the tumors treated with ACPP-HK2 were significantly smaller in volume than the control tumors injected with ACPP-SCR, thus demonstrating that our invention is at least capable of limiting tumor growth.

Figure 3:
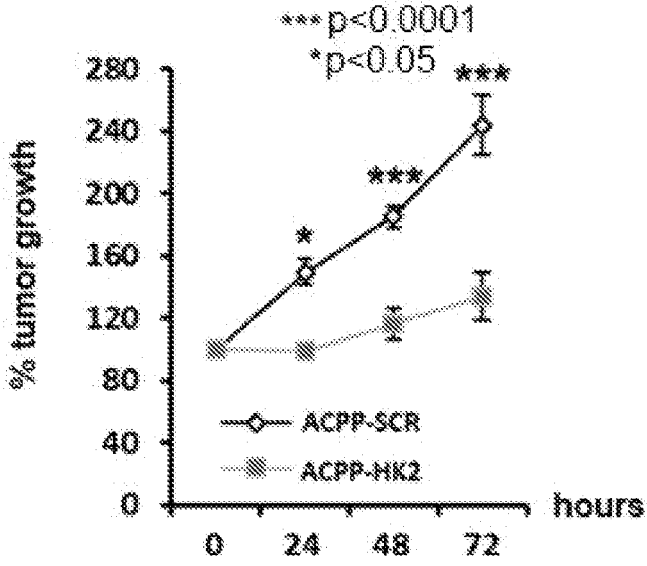
FIG. 3 reports the graph obtained by monitoring tumor growth after systemic treatment with isolated peptide having the sequence of SEQ ID NO:1

FIG. 3 shows the experimental data wherein two groups of mice were administered the ACPP-HK2 peptide or the ACPP-SCR peptide starting at 8 days post-inoculation every twelve hours up to the sixtieth hour. In this experiment, a double dose of peptides (60 nmoles/injection) was administered compared to the second experiment, again by intraperitoneal injection. At this dose, the injection of ACPP-HK2 strongly reduces, up to almost blocking, tumor growth.
In Vivo Tests: Breast Cancer In this experiment (FIG. 4), 200,000 murine breast cancer cell line 4T1 were injected subcutaneously into female mice. At 9 days post-inoculation of the cells, the mice were divided into two experimental groups and 60 nmoles of peptides (ACPP-HK2 or ACPP-SCR) dissolved in 500 µl of saline solution were injected intraperitoneally. The injections followed one the other every 12 hours up to 60 hours and at 72 hours the experiment ended. As in the previous experiment (FIG. 3), measurement of tumor masses shows that tumors treated with ACPP-HK2 are significantly smaller in volume than control tumors injected with ACPP-SCR. Also in this tumor model, tumor growth is almost blocked by ACPP-HK2.

In summary, our invention (isolated peptide of SEQ ID NO:1—ACPP-HK2) resulted to be effective in reducing tumor growth in different tumor models (FIGS. 1, 2, 3, and 4). In addition, our data show that, in mice, the preferable solution for carrying sequence HK2, or the peptide portion that performs cell death in tumor cells, is the intraperitoneal injection (FIG. 1).

Example 3

Histological Evaluation of Tissues

Figure 4:
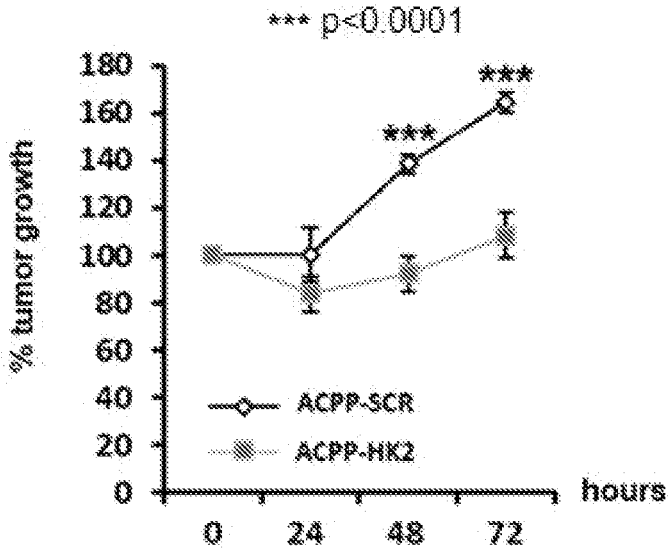
FIG. 4 shows the graph obtained by monitoring tumor growth after systemic treatment with the isolated peptide having the sequence of SEQ ID NO:1.
Figure 5:
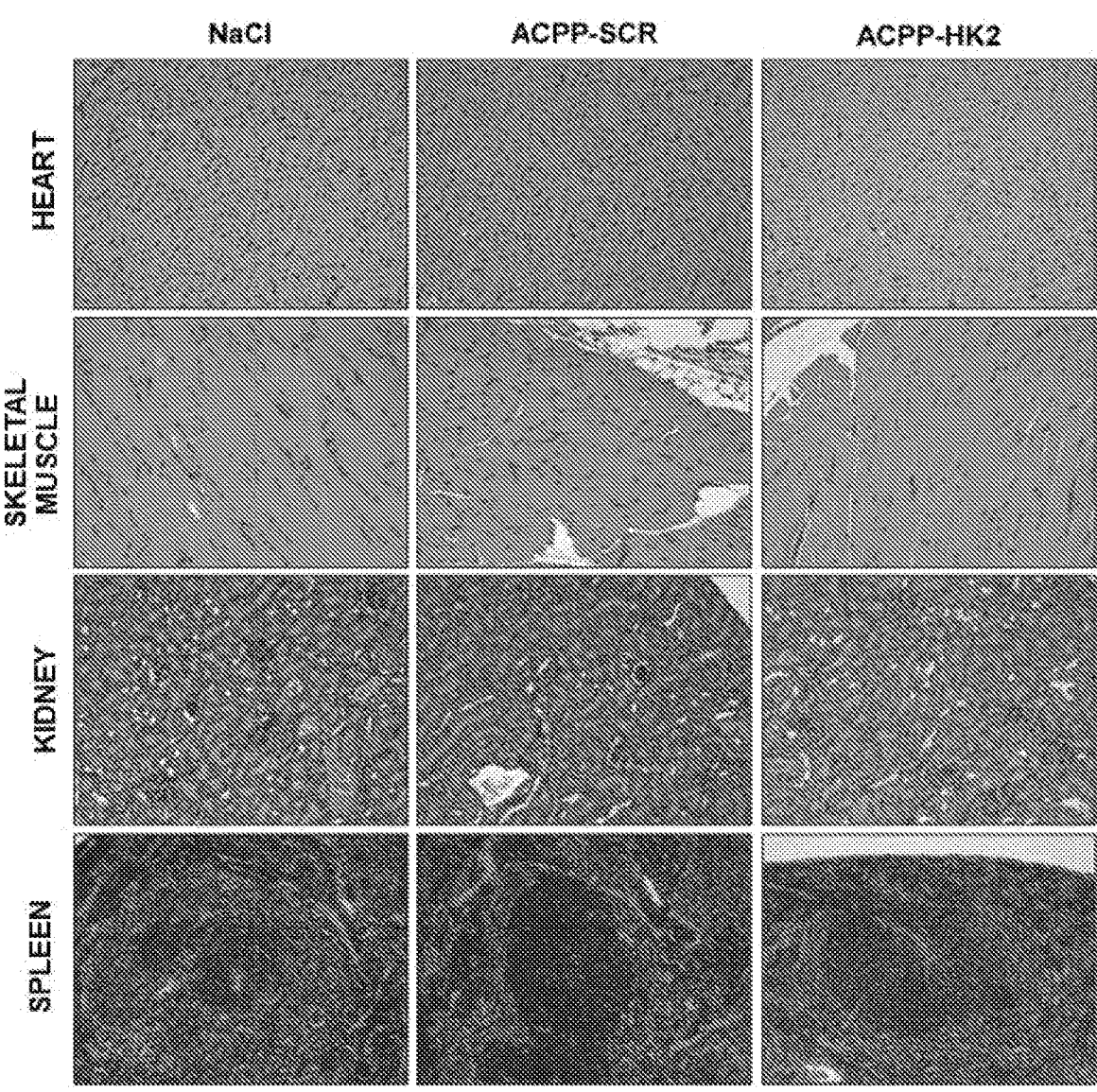
FIG. 5 reports examples of tissue samples from mice treated with the control peptide ACPP-SCR or with the isolated peptide having the sequence of SEQ ID NO:1.

At the end of each experiment shown in FIGS. 2, 3 and 4, and described in Example 2, male and female Balb/c mice underwent a complete autopsy with the assistance of an anatomopathologist expert. Subsequently, the histological analysis of most of the internal organs was carried out (the complete list is shown below, and some examples are shown in FIG. 5). The anatomopathologist expert assessed the histological characteristics of formalin-fixed sections of all the samples under a microscope, without finding any differences among different experimental groups (ACPP-SCR and ACPP-HK2) or any tissue alterations. The group of mice not receiving any peptide treatment (NaCl) acts as an additional control. The expert's conclusion is that the treatment with ACPP-HK2 has no toxic side effect neither for non-tumor tissues nor for the whole organism.

List of organs or tissues analyzed: heart, skeletal muscle, kidney, spleen, lung, liver, brain, intestine, pancreas, bone marrow, lymph nodes, thyroid gland, parathyroid glands, and adrenal glands.

In parallel, tumor samples deriving from the experiments shown in FIGS. 2, 3 and 4, and described in Example 2, were evaluated through immunohistochemical analysis using specific antibodies for HK2 and MMP2 (FIG. 10). HK2 and MMP2 protein expression after treatment with ACPP-HK2 does not vary as compared to treatment with ACPP-SCR or untreated. This indicates that the tumors do not undergo any form of adaptation (decrease or disappearance of the levels of the two molecules) that could affect the efficacy of the treatment.

Example 4

Ex Vivo Tests

Figures 6A, 6B:
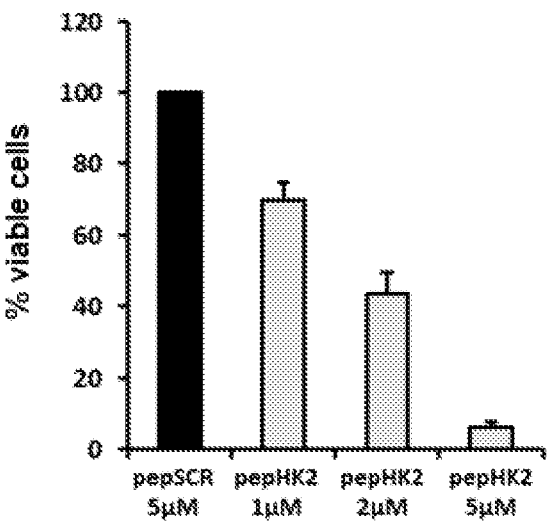
FIG. 6A shows the treatment of B-CLL cells freshly isolated from patient biopsies with the active portion of ACPP-HK2 (SEQ ID NO:1), named pepHK2, and with pepSCR (experimental control).
FIG. 6B shows B-CLL cell death induced by various concentrations of pepHK2 (dose/response analysis).

In this study, human tumor cells isolated following blood sampling from patients with B-cell type chronic lymphocytic leukemia (B-CLL) were used. They are to be considered a good model to evaluate the effect of the peptide in blood tumors. The cells are derived from patients who are not receiving any anti-neoplastic therapy yet. As shown in FIGS. 6A and 6B, the active form of the peptide, pepHK2, is very rapid and effective in inducing concentration-dependent death of most tumor cells in all the patients analyzed, regardless of the different pro-neoplastic genetic alterations present in each of them.

Figure 7A:
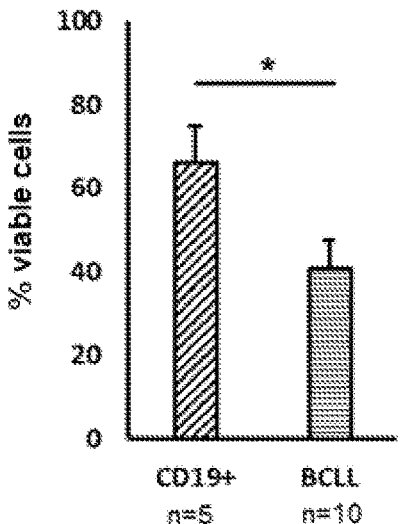
FIG. 7A reports experimental data in longer time periods.
Figure 7B:
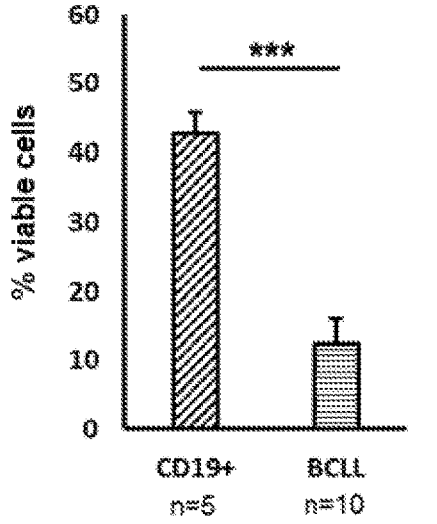
FIG. 7B reports experimental data in shorter time periods at a higher concentration of pepHK2.

To evaluate the possible toxicity of treatment with pepHK2, its effect on B-CLL cells viability was compared to the effect on the non-tumor counterpart, i.e. normal human B lymphocytes (CD19$^+$). Both cell types studied were derived from fresh biopsy specimens. CD19$^+$ B lymphocytes express HK2; therefore, as expected, pepHK2 decreases the viability of these cells, but with significantly lower efficacy and in longer times (FIGS. 7A and 7B) compared to the action it has on B-CLL cells. The fact that B lymphocytes from healthy subjects are less sensitive to pepHK2 clearly highlights the possibility of a therapeutic window for the use of ACPP-HK2. Furthermore, as described in the literature, B-CLL cells express greater amounts of MMP than non-tumor B lymphocytes. Hence, our invention could be very effective at low doses (prolonged over time) without any toxic effect for healthy cells, as demonstrated for solid tumors.

Example 5

Other In Vitro Models

Figure 8:
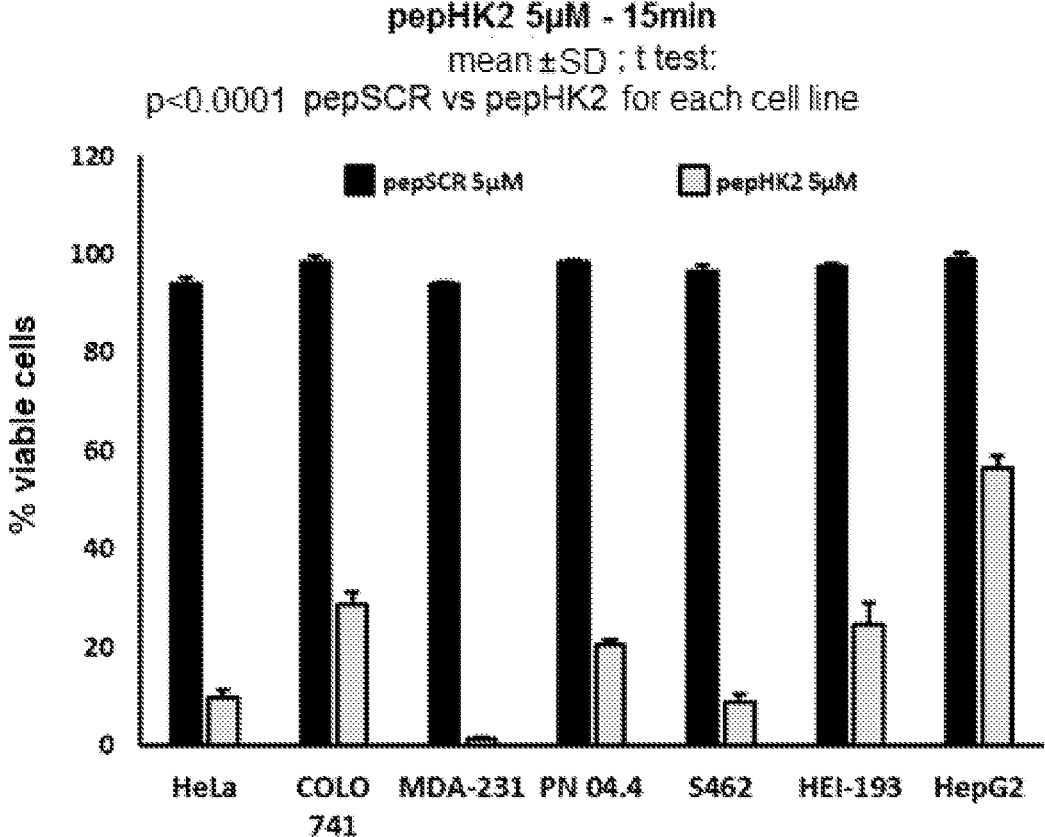
FIG. 8 shows the data of experiments in Example 6, wherein the viability of various cellular models originating from different human tumors after treatment with pepSCR and pepHK2 is represented.

The analysis of our anti-neoplastic strategy has therefore been extended to other human tumor types. FIG. 8 shows examples of response to the active form of ACPP-HK2 (pepHK2 5 µM) in cellular models resulting from cervical cancer (HeLa), colon cancer (COLO-741), breast cancer (MDA-231), plexiform neurofibroma (IFPN 04.4), malignant tumor of the peripheral nerve sheath (S462), schwannoma (HEI-193), and hepatocellular carcinoma (HepG2).

After 15 minutes of treatment, pepHK2 induces death of almost all the cells for all these tumor types, while the peptide with experimental control function (pepSCR, 5 μM) is ineffective. All cell models have proved highly sensitive to pepHK2 treatment, showing that our invention is effective in treating extremely heterogeneous tumor types, such as those listed in this example.

Example 6

Evidence of Anti HK2 Sequence Variants on Cancer Cells

FIGS. 9A and 9B report cell viability after treatment of tumor cells (HeLa cervical cancer cell line) at various concentrations and times with the peptides ACPP-HK2 (SEQ ID NO:1), ACPP-HK2 II (SEQ ID) NO: 8), ACPP-HK2 III (SEQ ID NO: 9) and ACPP-HK2 IV (SEQ ID NO:10). The results clearly demonstrate that all four tested peptides are able to decrease cell viability of cancer cells with different efficacy depending on concentration (between 5 and 50 μM) and treatment time (18 or 36 hours).

Example 7

Enzymatic Activity

FIG. 10A reports the enzymatic activity, i.e. the glucose phosphorylation capacity of purified recombinant human HK2 protein (hHK2) in the presence or absence of the active form of peptide ACPP-HK2. The results show that pepHK2 does not inhibit the enzyme activity. FIG. 10B shows the enzymatic activity of HK2, HK1 (ubiquitous isoenzyme in the body) and of both of them in the presence or absence of pepHK2 in extracts deriving from CT26 colon carcinoma cells and 4T1 breast carcinoma cells that were used for the in vivo experiments. Hexokinase enzymatic activity in tumor cells is not reduced by the active form of ACPP-HK2. This shows that the active form of the peptide ACPP-HK2, that penetrates the cells, does not reduce the glucose phosphorylation activity of the hexokinase family and therefore does not cause the systemic side effects found in other types of anti-HK2 treatment. From the detailed description and from the above examples, the advantages provided by the peptides of the present invention are evident. In particular, these peptides and their sequence variants have proven effective in the treatment of tumors without causing the general problems that arise with the anti-neoplastic strategies currently in use, such as systemic toxicity and lack of efficacy.

The invention claimed is:

1. An isolated peptide having a sequence selected from the group consisting of SEQ ID NO:1, SEQ ID NO:8, SEQ ID NO:9, and SEQ ID NO: 10, wherein said peptide allows:
    a) specific release of an active portion of a hexokinase 2 (HK2) protein in the proximity of neoplastic cells;
    b) penetration through a cell membrane; and/or
    c) rapid killing of tumor cells.

2. The isolated peptide according to claim 1, having the sequence of SEQ ID NO:1.

3. A method of using said peptide according to claim 1 in a subject in need thereof, said method comprising administering to said subject an effective amount of said peptide.

4. A method for treating a tumor, comprising the step of administering the peptide according to claim 1 to a subject in need thereof.

5. The method according to claim 4, wherein said tumor is a solid or liquid tumor.

6. The method according to claim 4, wherein said tumor is selected from the group consisting of colon cancer, breast cancer, leukemia, cervical and uterine cancer, plexiform neurofibroma, malignant tumor of the peripheral nerve sheath, schwannoma, and hepatocarcinoma.

7. The method according to claim 4, wherein said tumor is a tumor that expresses hexokinase type II.

8. The method according to claim 4, wherein said tumor is a metastatic tumor.

9. A pharmaceutical composition comprising the peptide according to claim 1, and a pharmaceutically acceptable vehicle.

10. The composition according to claim 9, in a solid or liquid form.

11. The composition according to claim 9, for enteral or parenteral administration by intravenous, intraperitoneal, oral, sublingual, aerosol, inhalation, spray, rectal, intraocular, topical, or transdermal administration routes.

* * * * *